United States Patent [19]
Bulard et al.

[11] Patent Number: 5,630,939
[45] Date of Patent: May 20, 1997

[54] FILTER ASSEMBLY DEVICE FOR USE IN SURGICAL ASPIRATED SUCTION

[75] Inventors: Ronald A. Bulard; Edward S. Gillespie, both of Ardmore, Okla.

[73] Assignee: Imtec Corporation, Ardmore, Okla.

[21] Appl. No.: 528,573

[22] Filed: Sep. 15, 1995

[51] Int. Cl.$^6$ ................................. B01D 35/02
[52] U.S. Cl. ................. 210/416.1; 210/448; 433/92; 604/319; 604/406
[58] Field of Search .................. 210/416.1, 448; 604/4, 319, 403, 49, 902, 406, 48; 433/92

[56] References Cited

U.S. PATENT DOCUMENTS

| | | | |
|---|---|---|---|
| 602,572 | 4/1898 | Browne et al. | 433/92 |
| 1,353,587 | 9/1920 | Heck | 433/92 |
| 2,530,283 | 11/1950 | Brown | 210/448 |
| 3,382,984 | 5/1968 | Kuss | 210/448 |
| 3,476,144 | 11/1969 | Krantz | 433/92 |
| 3,484,941 | 12/1969 | Svard | 433/92 |
| 3,785,380 | 1/1974 | Brumfield | 128/276 |
| 3,890,712 | 6/1975 | Lopez | 433/92 |
| 4,018,686 | 4/1977 | Shufflebarger et al. | 210/448 |
| 4,083,706 | 4/1978 | Wiley | 55/385 R |
| 4,468,217 | 8/1984 | Kuzmick et al. | 604/48 |
| 4,886,492 | 12/1989 | Brooke | 604/49 |
| 4,915,691 | 4/1990 | Jones et al. | 604/73 |
| 5,078,603 | 1/1992 | Cohen | 433/91 |
| 5,192,439 | 3/1993 | Roth et al. | 210/416.1 |
| 5,358,638 | 10/1994 | Gershenson | 210/448 |

*Primary Examiner*—Cynthia L. Nessler
*Attorney, Agent, or Firm*—Dunlap & Codding, P.C.

[57] ABSTRACT

A filter assembly for elective use in conjunction with a surgical evacuation system is provided which includes a filter housing having a head portion and a body portion with a through passageway extending therebetween defining a filter receiving chamber. The head portion is connectable to an aspirator tip and the body portion is connectable to a flexible suction conduit. A filter element is disposed within the filter receiving chamber of the filter housing. The filter element includes a head member having a fluid flow passageway extending therethrough, a fluid impermeable base member spatially disposed from the head member and a fluid permeable body member disposed between the head member and the base member. The head member has a diameter greater than the base so that a portion of the head member extends outwardly from the body portion of the filter housing to enhance removal of the filter element and a second portion of the head member forms a substantially fluid-tight seal with the body portion of the filter housing.

6 Claims, 2 Drawing Sheets

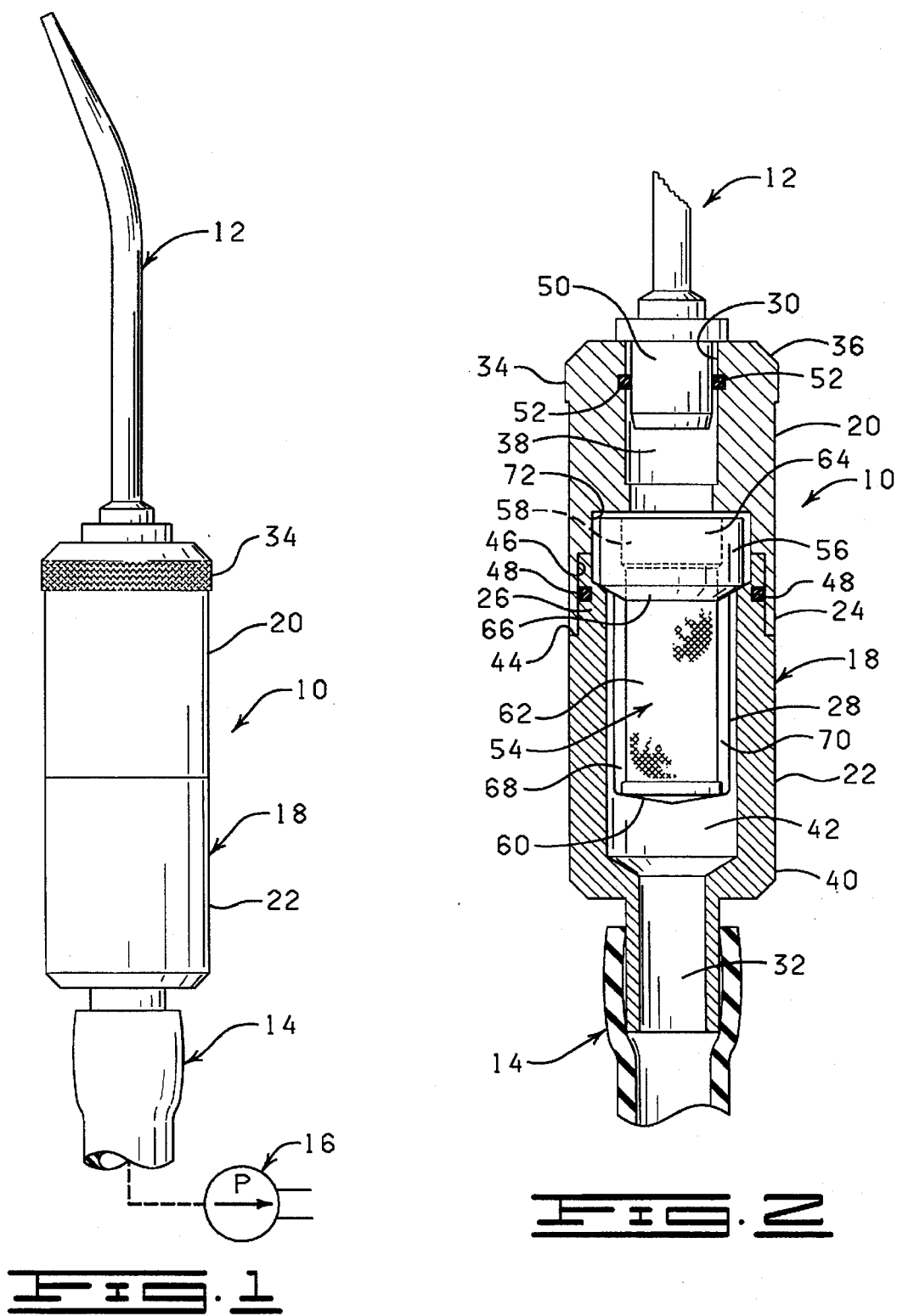

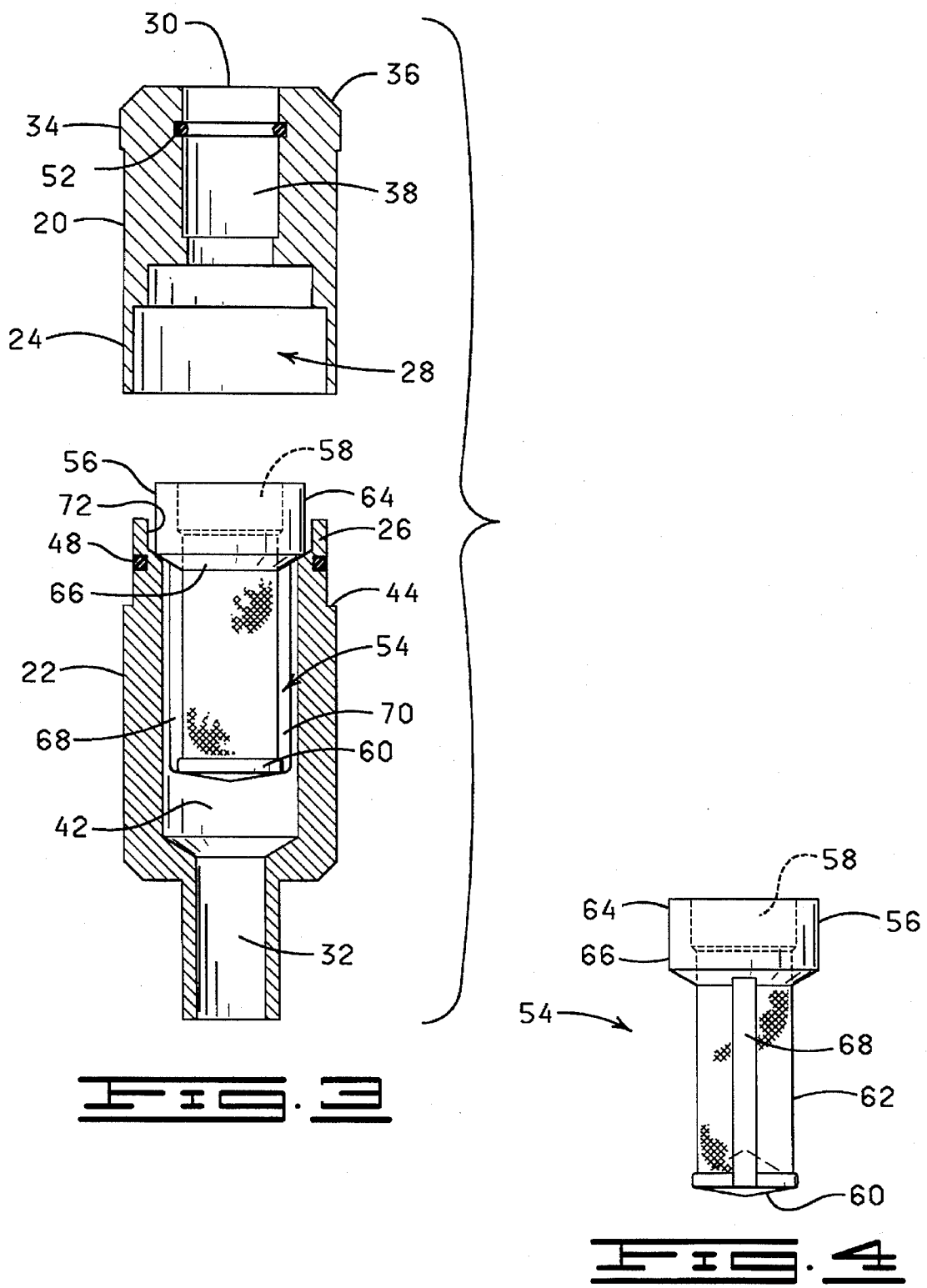

FILTER ASSEMBLY DEVICE FOR USE IN SURGICAL ASPIRATED SUCTION

BACKGROUND AND SUMMARY OF THE INVENTION

This invention relates to a filtering assembly, and more particularly but not by way of limitation, to a filter assembly for the collection of aspirated tissue or materials during surgical procedures.

A standard adjunct to all modern surgical procedures is the use of suction pump aspirating systems. The almost immediate removal of human or introduced fluids from the surgical site by use of an aspirator tip, tubing and suction pump provides the clinician vastly improved visibility and dexterity throughout the treatment procedure. One inherent disadvantage to a suction pump aspirating system is the inability to retrieve, collect or save fine human or foreign materials once captured at the aspirating end.

An important function of the present invention is to permit the clinician to easily introduce a fine filter assembly into the aspirator line of a suction pump aspirating system to preclude the loss of valuable materials, tissue or information. Valuable materials, such as precious dental alloys, may also be collected and recycled; and human tissues may be collected for medical biopsy purposes.

Another use of the present invention is for autologous transfer of collected human tissue to another needed or more desirable site. Critical information may be gathered by the use of the filter assembly of the invention. Use of the filter assembly will immediately visually verify if certain undesirable pathological or foreign bodies have been successfully and completely removed. These might include detached tooth root tips, metal particles from a wound injury, or cystic membrane walls. Also verifiable would be the accidental, inadvertent removal of healthy human tissue. The use of the filter assembly of the present invention in collecting diagnostic data will in some cases eliminate or reduce the necessity of patient exposure to additional diagnostic radiation. Likewise, the knowledge gained may preclude unnecessary exploratory tissue trauma.

Yet another clinical application of the filter assembly of the present invention is the quick, verifiable retrieval of mechanical components utilized in surgical procedures. The possibility of contracting or introducing vital or bacterial infections has almost universally mandated the use of surgical gloves in all medical fields during the past ten years. A major disadvantage of glove use is the reduction of tactile sensation. Dental/medical devices of minute dimensions are now routinely used in bone fixation, dental implantology, endontics, tooth pin and post reconstruction to mention only a few. Metal screws, pins and posts may become loose in the surgical opening or oral cavity. By use of the filter assembly of the present invention, such components may be quickly extracted by the suction device. The filter verifies complete retrieval. Additionally, such items as broken surgical drills or other mechanical or human debris may be verifiably removed by use of the filter assembly of the present invention. When captured and retrieved, visual verification will be certain and almost instantaneous. The necessity of additional exploratory probing trauma, diagnostic testing or radiographic examination become unnecessary.

In accordance with the present invention, a filter assembly for elective use in conjunction with a surgical evacuation system (i.e., an aspirator tip, a flexible suction conduit and a suction pump) is provided which comprises a filter housing having a head portion and a body portion. The head portion is characterized as having a first end, a second end and a through passageway extending therebetween and the first end of the head portion is connectable to the aspirator tip so that fluid communication is provided between the aspirator tip and the passageway extending through the head portion. A portion of the passageway in the second end of the head portion of the filter housing defines a first chamber.

The body portion of the filter housing is also characterized as having a first end, a second end and a through passageway extending therebetween. The second end portion of the body portion is connectable to the flexible suction conduit and a portion of the passageway in the first end of the body portion defines a second chamber such that when the first end of the body portion is slidably disposed in the second end of the head portion, the first and second chambers in the head portion and the body portion cooperate to define a filter receiving chamber.

A removable, elongated mesh filter element is disposed within the filter receiving chamber. The filter element comprises a head member having a fluid flow passageway extending therethrough, a fluid impermeable base member spatially disposed from the head member and a fluid permeable mesh body member extending between the head member and the base member. The head member is provided with a diameter greater than the base member so that when the filter element is disposed within the filter receiving chamber, a first portion of the head member extends outwardly from the second chamber of the body portion of the filter element so as to enhance removal of the filter element and a second portion of the head member extends into the second chamber of the body portion so that a fluid-tight seal is formed therebetween. Thus, the fluid mesh permeable body member of the filter element provides a collection chamber for aspirated tissue and materials during surgical procedures.

In one aspect, the elongated filter element of the filter assembly of the present invention is further provided with reinforcing members extending between the head member and the base member of the filter element so as to enhance the rigidity of the fluid permeable mesh body member of the filter element and thereby enhance insertion and removal of the filter element from the filter receiving chamber defined by the filter housing.

An object of the present invention is to provide a filter assembly which may be readily inserted and removed from an evacuation system between an aspirator and a suction line of a suction pump aspirating system.

Another object of the present invention is to provide a filter assembly for use in a suction pump aspirating assembly which permits easy and rapid disassembly for removal of the filter from the filter assembly.

Still another object of the invention is to provide a filter assembly for use in a suction pump aspirating assembly which is economical to manufacture, versatile in use and which can be readily cleaned and sterilized.

Other objects, advantages and features of the present invention will become apparent to those skilled in the art from a reading of the following detailed description in conjunction with the drawings and the appended claims.

BRIEF DESCRIPTION OF THE DRAWINGS

FIG. 1 is an elevational view of a filter assembly of the present invention disposed between an aspirator and tubing of a suction pump aspirating system.

FIG. 2 is a cross-sectional view of the filter assembly of FIG. 1.

FIG. 3 is a cross-sectional view of the filter assembly of FIG. 1 having a filter disposed within a filter receiving chamber of a filter housing, the filter housing being illustrated in a disassembled condition to more clearly illustrate the positioning of the filter therein.

FIG. 4 is an elevational view of the filter of the filter assembly of the present invention.

DESCRIPTION OF ILLUSTRATIVE EMBODIMENTS

Referring now to the drawings, and more particularly to FIGS. 1 and 2, shown therein is a filter assembly 10 constructed in accordance with the present invention for use in conjunction with a surgical evacuation system which comprises an aspirator tip 12, a suction conduit 14 and a suction pump 16. The filter assembly 10 may be machined from a variety of metals or autoclavable plastics or injection molded of autoclavable plastics. The design may also vary in size to accommodate any surgical situation from minute craniofacial surgical applications to veterinary large animal surgical applications. Further, as will be described in more detail hereinafter, the filter assembly 10 can be readily disassembled for thorough cleaning and sterilization.

The filter assembly 10 is provided with a filter housing 18 having a head portion 20 and a body portion 22. A second or lower end 24 of the head portion 20 frictionally receives a first or upper end 26 of the body portion 22 so as to define a filter receiving chamber 28 (FIG. 2) therebetween. An aspirator accepting opening 30 openly communicates with the filter receiving chamber 28 and a filter chamber exit opening 32 of the filter housing 18 so that fluid flow is provided through the filter receiving chamber 28 when the head portion 20 and the body portion 22 of the filter housing 18 are in a connected position as illustrated in FIGS. 1 and 2.

As more clearly shown in FIG. 1, the head portion 20 of the filter housing 18 is provided with a peripheral area 34 of enlarged diameter to enhance gripping of the head portion 20 of the filter housing 18 during either securing of the head portion 20 to the body portion 22 or removal of the head portion 20 from the body portion 22. The peripheral area 34 of enlarged diameter is desirably tactily enhanced with multiple serrations or machine knurl patterns to enhance the purchase of the head portion 20 and to promote ease of use during surgical aspiration.

The filter housing 18 can be manufactured from any acceptable machined metals or from surgically approved plastic materials. Further, the size of the filter housing 18 can vary widely. However, desirable results have been obtained wherein the filter housing 18 is approximately 1 inch in diameter and approximate 4 inches long. It should be understood that by utilizing the same or similar designs, other sizes can be manufactured to accept different sizes of filters, the size of the filter housing 18 depending upon whether the surgical requirements are minute, craniofacial surgeries or veterinary large animal applications.

Referring more specifically to FIGS. 2 and 3, the head portion 20 of the filter housing 18 is characterized as having a first or upper end 36, the second or lower end 24, and a through passageway 38 extending therebetween. The first end 36 of the head portion 20 is connectable to the aspirator tip 12 such that fluid communication is provided between the aspirator tip 12 and the passageway 38 extending through the head portion 20.

The body portion 22 of the filter housing 18 is also characterized as having the first end 26, a second end 40, and a through passageway 42 extending therebetween. The upper end 26 of the body portion 22 of the filter housing 18 defines a shoulder step 44 which mates into a counterbore 46 of the head portion 20 of the filter housing 18 so as to provide a sliding sealed fit therebetween. The union of the head portion 20 to the body portion 22 of the filter housing 18 can be further facilitated by the use of a "O" ring 48 disposed in a recess formed about the external surface of the body portion 22 of the filter housing 18 near the first end 26 thereof substantially as shown so that a fluid-tight seal is formed between the head portion 20 and the body portion 22.

Once the head portion 20 is mated with the body portion 22, a through chamber opening is formed through the filter housing 18, the aspirator accepting opening 30, and the passageway 38 in the head portion 20, the passageway 42 at the filter chamber exit opening 32 in the body portion 20.

As more clearly shown in FIG. 2, the aspirator tip 12 is provided with an aspirator fitting 50 whose outside diameter is slightly smaller than the aspirator accepting opening 30 in the first end 36 of the head portion 20. The aspirator fitting 50 can be disposed in a locked sealed position inside the aspirator accepting opening 30 and retained therein by an internally disposed "O" ring 52 substantially as shown whereby a substantially fluid-tight seal is formed between the head portion 20 of the filter housing 18 and the aspirator tip 12 via the aspirator fitting 50 and the "O" ring 52. The filter housing 18 is now conjoined and ready for use with or without a filter element 54 in place.

Referring now to FIGS. 2–4, the filter element 54 which is disposable within the filter receiving chamber 28 of the filter housing 18 is a substantially rigid, elongated element comprising an enlarged head member 56 having a fluid flow passageway 58 extending therethrough, a fluid impermeable base member 60 spatially disposed from the head member 56 and a substantially tubular-shaped fluid permeable body member 62 disposed between the head member 56 and the base member 60. The fluid flow passageway 58 extending through the head member 56 is provided with an internal diameter at least equal to an internal diameter of the aspirator accepting opening 30 in the first end 36 of the head portion 20 of the filter housing 18. Desirably, the fluid permeable body member 62 of the filter element 54 is fabricated of a substantially rigid mesh material fabricated from metal, polymeric materials or combinations thereof. The mesh size of the mesh material used in the fabrication of the fluid permeable body member 62 of the filter element 54 can vary depending on the desired use of the filter assembly 10.

The head member 56 is provided with a sufficient height such that when the filter element 54 is disposed in the filter receiving chamber 28 of the filter housing 18, a first portion 64 of the head member 56 extends outwardly from the filter receiving chamber 28 defined by the body portion 22 of the filter housing 18 so as to enhance removal of the filter element 54. A second portion 66 of the head member 56 extends into portion of the filter receiving chamber 28 defined by the body portion 22 so that a fluid-tight seal is formed therebetween which permits the fluid permeable body member 62 of the filter element 54 to function as a collection chamber for aspirated tissue and materials during surgical procedures.

To enhance the rigidity of the fluid permeable body member 62, the filter element 54 further comprises reinforcing members 68 and 70 which extend between the head member 56 and the base member 60 of the filter element 54.

The reinforcing members 68 and 70 enhance the rigidity of the fluid permeable body member 62 of the filter element 54 and enhance insertion of the filter element 54 into the filter receiving chamber 28 defined by the filter housing 18, as well as removal of the filter element 54 therefrom.

To enhance a substantially fluid-tight seal between the head member 56 of the filter element 54 and the first end 26 of the body portion 22 of the filter housing 18, the first end 26 of the filter housing 18 extending about the passageway 42 is flared or beveled outwardly; and the lower surface of the second portion 66 of the head member 56 is beveled. Thus, when the filter element 54 is slidingly disposed in the filter receiving chamber 28 of the body portion 22 of the filter housing 18, the beveled portion of the head member 56 engages the flared portion of the body portion 22 to provide an effective seal therebetween. That is, the filter receiving chamber 28 has an inside diameter which is slightly larger than the diameter across the longitudinal filter reinforcing arms 68, 70 and fluid permeable body member 62 of the filter element 54, but smaller that the head member 56 of the filter element 54. However, the filter receiving chamber 28 is provided with a counterbore 72 at the junction of the head portion 20 and the body portion 22 which is slightly larger than the head member 56 substantially as shown in FIGS. 2 and 3, but tapers to provide the beveled surface. This unique feature enables an effective seal to be formed about the head member 56 of the filter element 54 and the body portion 22 of the filter housing 18 while at the same time permitting a portion of the head member 56 to extend upwardly therefrom when the filter element 54 is seated in the filter receiving chamber 28. As previously stated, by having the portion of the head member 56 exposed, placement of the filter element 54 is enhanced as well as removal of the filter element 54 by permitting sure and firm purchase of the head member 56 of the filter element 54 when the head portion 20 of the filter housing 18 is disconnected from the body portion 22.

The filter housing 18 may be utilized without the filter element 54 as a convenient handle adjunct for the aspirator tip 12 and the flexible suction conduit 14, or, as preferred, the filter element 54 will be disposed within the filter receiving chamber 28 defined by the head portion 20 and the body portion 22 of the filter housing 18. It should be noted that, in the event the filter housing 18 is employed initially without the filter element 54 in place, if at any point during the surgical procedure when the use of the filter element 54 is required or anticipated, it may be quickly and easily introduced in the following manner: The head portion 20 of the filter housing 18 is separated from the body portion 22 by a twisting, sliding motion to reveal the filter receiving chamber 28. The head member 56 of the filter element 54 is purchased by a thumb and forefinger or some surgical grasping instrument. The filter element 54 is then slid easily into the filter receiving chamber 28 whose diameter is slightly larger than the diameter across the base member 60, the fluid permeable body member 62 and the longitudinal reinforcing members 68, 70 of the filter element 54, but smaller than the head member 56 of the filter element 54. The counterbore 72 at the entrance of the filter receiving chamber 28 is slightly larger than the head member 56 of the filter element 54 and is configured to accept the head member 56 and secure same in a stable position. It is critical and unique to the present invention that the first portion 64 of the head member 56 be exposed when the filter element 54 seats completely in the filter receiving chamber 28. The advantages of having the first portion 64 of the head member 56 of the filter element 54 exposed enhances removal of the filter element 54 by sure and firm purchase, whereas, when the filter element 54 is in position within the filter receiving chamber 28 of the filter housing 18, fluids and particulate matter unrestrictedly pass through the filter element 54 so that unwanted fluids can exit through the fluid permeable body member 62 of the filter element 54 while valuable human tissues, pathological tissues for analysis, precious metals, and the like are captured within the fluid permeable body member 62. Further, because the body portion 22 of the filter housing 18 allows for certain, external purchase of the head member 56 for retrieval of the filter element 54, the possibility of spillage and loss of the materials sought to be collected in the filter element 54 is substantially eliminated. Thus, once the filter element 54 is removed from the filter receiving chamber 28, the enclosed materials may be transferred to a suitable receptacle and the filter element 54 may then be reinserted, a replacement filter element 54 be inserted, or the procedure reinitiated without the use of the filter element 54, at the discretion of the clinician. As can be seen in FIGS. 2 and 3, when the filter element 54 is completely seated in the filter receiving chamber 28 of the body portion 22 of the filter housing 18, the filter element 54 becomes totally captured by the head seating flat of the head portion 20 of the filter housing 18, the counterbore 72 and the filter receiving chamber 28 of the body portion 22 of the filter housing 18.

While the filter housing 18 and the filter element 54 are illustrated as having a circular configuration, it should be understood that the filter housing 18 and the filter element 54 can be of any variety of geometric shapes, such as oval, circular with longitudinal flats, squares and the like.

Changes may be made in the construction and the operation of the various parts, elements and assemblies described herein and the steps or the sequence of steps of the methods described herein without departing from the spirit and the scope of the invention as defined in the following claims.

What is claimed:

1. A filter assembly for use in conjunction with a surgical evacuation system comprising an aspirator tip, a flexible suction conduit and a suction pump, the filter assembly comprising:

a filter housing comprising a head portion and a body portion, the head portion having a first end, a second end and a through passageway extending therebetween, the first end of the head portion connected to the aspirator tip and fluidly communicating the aspirator tip with the passageway extending through the head portion, a portion of the passageway in the second end of the head portion of the filter housing defining a first chamber, the body portion having a first end, a second end and a through passageway extending therebetween, the second end of the body portion connected to the flexible suction conduit, a portion of the passageway in the second end of the body portion defining a second chamber such that when the first end of the body portion is slidingly disposed in the second end of the head portion the first and second chambers in the head portion and the body portion cooperate to define a filter receiving chamber; and a removable, elongated tubular mesh filter element disposed within the filter receiving chamber of the filter housing, the filter element comprising a head member having a fluid flow passageway extending therethrough, a fluid impermeable base member spatially disposed from the head member and a fluid permeable tubular mesh body member disposed between the head member and the based member, the head member having a first portion and a second portion, said first portion of the head member extending beyond the first end of the body portion of the filter body to facilitate removal of the filter element from the filter housing when the head portion of the filter housing is separated from the body portion of the filter housing and said second portion of the head member forming a substantially fluid-tight seal with the body portion of the filter housing whereby the fluid permeable tubular mesh body member of the filter element provides a collection chamber for aspirated tissue and materials during surgical procedures.

2. The filter assembly of claim 1 wherein the elongated filter element further comprises reinforcing members extending between the head member and the base member of the filter element so as to enhance the rigidity of the fluid permeable mesh body member of the filter element and enhance insertion of the filter element into the filter receiving chamber defined by the filter housing as well as removal of the filter element therefrom.

3. The filter assembly of claim 2 wherein the head member, the base member and the reinforcing members of the filter element are constructed of plastic, metal and combinations thereof.

4. The filter assembly of claim 3 wherein the filter housing is constructed of plastic, metal and combinations thereof.

5. The filter assembly of claim 1 wherein the filter assembly further comprises aspirator connector means for connecting the aspirator tip to the head portion of the filter housing such that a substantially fluid-tight seal is formed therebetween.

6. The filter assembly of claim 5 further comprising sealing means for providing a fluid-tight seal between the head portion and the body portion of the filter housing when same are in a connected position.

* * * * *